(12) United States Patent
Cho et al.

(10) Patent No.: US 9,156,851 B2
(45) Date of Patent: Oct. 13, 2015

(54) PHOTOCURABLE DIANHYDRO-HEXANE-HEXOL DERIVATIVE, MANUFACTURING METHOD THEREOF, AND PHOTOCURABLE COMPOSITION INCLUDING SAME

(75) Inventors: Jin Ku Cho, Gyeonggi-do (KR); Baek Jin Kim, Chungcheongnam-do (KR); Sang Yong Kim, Chungcheongnam-do (KR); Seung Han Shin, Seoul (KR); Jae Won Jeong, Seoul (KR); Bo Ra Kim, Daejeon (KR)

(73) Assignee: KOREA INSTITUTE OF INDUSTRIAL TECHNOLOGY, Chungcheongnam-do (KR)

( * ) Notice: Subject to any disclaimer, the term of this patent is extended or adjusted under 35 U.S.C. 154(b) by 0 days.

(21) Appl. No.: 14/110,457

(22) PCT Filed: Dec. 29, 2011

(86) PCT No.: PCT/KR2011/010293
§ 371 (c)(1),
(2), (4) Date: Oct. 8, 2013

(87) PCT Pub. No.: WO2012/157832
PCT Pub. Date: Nov. 22, 2012

(65) Prior Publication Data
US 2014/0073716 A1  Mar. 13, 2014

(30) Foreign Application Priority Data

May 19, 2011 (KR) ........................ 10-2011-0047396

(51) Int. Cl.
| | |
|---|---|
| C08F 2/46 | (2006.01) |
| C08F 2/50 | (2006.01) |
| C08G 61/04 | (2006.01) |
| C07D 493/04 | (2006.01) |
| C08F 136/20 | (2006.01) |

(52) U.S. Cl.
CPC ............ *C07D 493/04* (2013.01); *C08F 136/20* (2013.01)

(58) Field of Classification Search
None
See application file for complete search history.

(56) References Cited

U.S. PATENT DOCUMENTS

| | | | | |
|---|---|---|---|---|
| 3,041,300 | A * | 6/1962 | Morrison | 523/402 |
| 3,272,845 | A * | 9/1966 | Zech et al. | 549/464 |
| 5,788,880 | A | 8/1998 | Schierlinger et al. | |
| 2002/0013482 | A1 | 1/2002 | Brader et al. | |
| 2005/0124762 | A1* | 6/2005 | Cohen et al. | 525/191 |
| 2008/0009599 | A1 | 1/2008 | East et al. | |
| 2012/0172282 | A1* | 7/2012 | Breffa et al. | 510/506 |
| 2014/0249285 | A1* | 9/2014 | Palmese et al. | 526/268 |

FOREIGN PATENT DOCUMENTS

| | | |
|---|---|---|
| JP | 06-261774 | 9/1994 |
| WO | WO 89/005302 | 6/1989 |

OTHER PUBLICATIONS

Chheda, J.N. et al., Liquid-Phase Catalytic Processing of Biomass-Derived Oxygenated Hydrocarbons to Fuels and Chemicals, Angew. Chem. Int. Ed. 2007, 46, 7164-7183.
Corma, A. et al., Chemical Routes for the Transformation of Biomass into Chemicals, Chem. Rev. 2007, 107, 2411-2502.
International Search Report mailed on Sep. 27, 2012 for International Application No. PCT/KR2011/010293.

* cited by examiner

*Primary Examiner* — Ling Choi
*Assistant Examiner* — Jessica E Whiteley
(74) *Attorney, Agent, or Firm* — Pearl Cohen Zedek Latzer Baratz LLP

(57) ABSTRACT

Provided herein is a photocurable dianhydrohexanehexol derivative, a method preparing the same, and a composition including the same, for example, to a photocurable compound derived from environmentally friendly biomass, the compound having a structure where a 2-hydroxypropyl methacrylate (HPM) functional group prepared by reacting a biomass derived dianhydrohexanehexol (1,4:3,6-dianhydro-d-hexane-1,2,3,4,5,6-hexol, DHH) compound under an optimal reaction condition is combined, a preparing method thereof, and a photocurable composition comprising the photocurable compound.

20 Claims, 5 Drawing Sheets

PHOTOCURABLE DIANHYDRO-HEXANE-HEXOL DERIVATIVE, MANUFACTURING METHOD THEREOF, AND PHOTOCURABLE COMPOSITION INCLUDING SAME

CROSS-REFERENCE TO RELATED APPLICATIONS

This application is a National Phase Application of PCT International Application No. PCT/KR2011/010293, filed Dec. 29, 2011, claiming the benefit of Korean Patent Applications No. 10-2011-0047396, filed May 19, 2011, which are hereby incorporated by reference.

BACKGROUND

1. Field

The following description relates to a photocurable dianhydrohexanehexol derivative, a method preparing the same, and a composition including the same, for example, to a photocurable compound derived from environmentally friendly biomass, the compound having a structure where a 2-hydroxypropyl methacrylate (HPM) functional group prepared by reacting a biomass derived dianhydrohexanehexol (1,4:3,6-dianhydro-d-hexane-1,2,3,4,5,6-hexol, DHH) compound under an optimal reaction condition is combined, a preparing method thereof, and a photocurable composition comprising the photocurable compound.

2. Description of Related Art

Curable materials such as adhesive, glue, sealant, coating, encapsulant, and paint etc. are used in various industrial areas including civil engineering, architecture, paving, bookbinding, electronics, precision, optical products, carpentry, plywood, textile, leather, and medical treatment. These are used in increasingly wide range of areas.

These curable materials are prepared in the form of a mixture having chemical materials with synthetic resin as the main material. And they generate harmful chemical materials such as volatile organic chemicals (VOC), dioxin, and endocrine disruptors due to various volatile additives that are added to enhance the organic solvents used in the preparing processes and properties.

Recently, environmental regulations of international treaties are placing strict limitations on production and use of such harmful materials, and furthermore, EU is utilizing these regulations as a new means for trade sanctions. In step with this trend, conventional solvent-based adhesives are being replaced by water soluble, solvent free type, and hot melt type adhesives.

Meanwhile, most of the fine chemical materials that we currently use including the aforementioned curable materials are petrochemicals derived from oil refinery processes. However international oil prices are steadily increasing due to reduced oil reserves and sudden increase of demand mainly from BRICs, and as international treaties that strictly regulate emission of greenhouse gases take effect, use of irreversible fossil resources such as petroleum is expected to cause significant amount of environmental costs.

Therefore, much effort is being made to obtain conventional-oil resources-derived fine chemical products from new resources, and a case in point is using carbohydrate biomass as a source of supply. (Ghheda, J. N. et a; *Angew. Chem. Int. Ed.* 2007, 46, 7164-7183, Corma, A. et al., *Chem. Rev.* 2007, 107, 2411-2502)

The natural world produces a significant amount of carbohydrate of about 170 billion tons each year, and humans use only about 3% of it for food, paper, furniture, and building materials. Therefore, fine chemical products prepared from carbohydrate biomass that is renewable and can be sustainably used are expected to replace petrochemical products.

Meanwhile, of the compounds derived from oil resources, bisphenol A is a material used as the starting material of various chemical materials. It is applied to polycarbonate and various curable materials.

However, bisphenol A is a toxic material that causes the problem of endocrine disruptor. And recently, bisphenol A polycarbonate used in baby feeding bottles is being thrown out from the markets.

Accordingly, many attempts are being made to replace bisphenol A, and the most representative one is dianhydrohexanehexol derived from carbohydrate biomass (1,4:3,6-dianhydro-hexane-1,2,3,4,5,6-hexol, DHH).

Polycarbonate prepared by using isosorbide which is an isomer of DHH, instead of bisphenol A, is already being applied to lens in eyeglasses.

Accordingly, the present inventors conducted research considering the aforementioned, and as a result, by reacting a biomass-derived dianhydrohexanehexol compound under optimal reacting conditions, succeeded in preparing a compound where a 2-hydroxypropyl methacrylate (HPM) functional group is combined. They completed the present invention by ascertaining the capability of providing a photocurable compound having a biomass-derived DHH frame which may replace a bisphenol A compound derived from conventional oil resources with a photocurable compound derived from environmentally friendly biomass, and which has not only high yield rates and economic feasibility, but also fast curing speeds.

SUMMARY

Therefore, the purpose of the present disclosure is to provide a photocurable compound having a 1,4:3,6-dianhydrohexane-1,2,3,4,5,6-hexol (DHH) frame derived from environmentally friendly biomass, the compound capable of replacing bisphenol A photocurable materials derived from oil resources which generate conventional harmful materials.

Another purpose of the present disclosure is to provide a photocurable compound having a biomass-derived DHH frame, the compound having a high yield rate and highly economical synthesizing route.

Yet another purpose of the present disclosure is to provide a photocurable composition containing a photocurable compound derived from the aforementioned biomass.

In one general aspect, there is provided a compound denoted by the following chemical formula 1.

[Chemical formula 1]

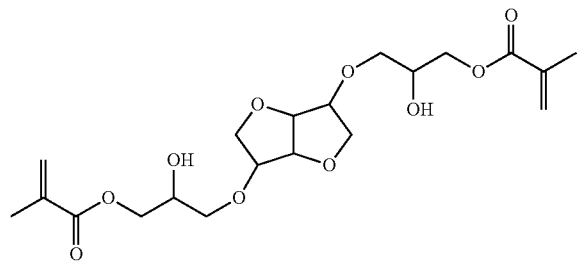

In the general aspect, the compound denoted by the chemical formula 1 may be a photocurable compound having a biomass-derived dianhydrohexanehexol(1,4:3,6-dianhydrohexane-1,2,3,4,5,6-hexol, DHH) frame consisting of a molecular structure where two 2-hydroxypropyl methacrylate (HPM) functional groups are combined.

In the general aspect of the compound, the biomass-derived dianhydrohexanehexol used for providing the DHH frame may have a structure of the following chemical formula 2.

[Chemical formula 2]

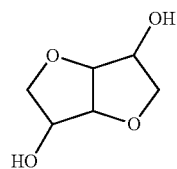

That is, in the general aspect, there is provided a material that may replace bisphenol A that is derived from oil resources and is known as a toxic material by applying a DHH compound (chemical formula 2) derived from carbohydrate biomass.

In the general aspect, the DHH compound (chemical formula 2) may have a firm ring structure, and thus may have similar physical features as bisphenol A generated in an oil chemical process and may be used as an alternative compound.

By applying a glycidyl functional group to the DHH compound to obtain a compound that is denoted by the following chemical compound 3 and then reacting the compound with methacrylic acid, thereby providing a photocurable compound (chemical formula 1) where two HPM functional groups are combined with a DHH frame, there is provided not only various functions of only firm properties due to the heterocyclic compound structure but also adhesive capability due to the hydroxyl group existing inside the molecule and photocuring capability due to the methaclyrate functional group.

[Chemical formula 3]

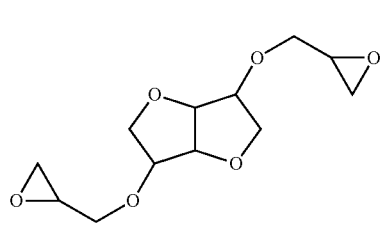

In addition, in another general aspect, there is provided a method for preparing a compound denoted by the following reaction formula 1.

[Reaction formula 1]

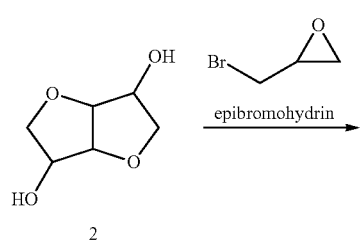

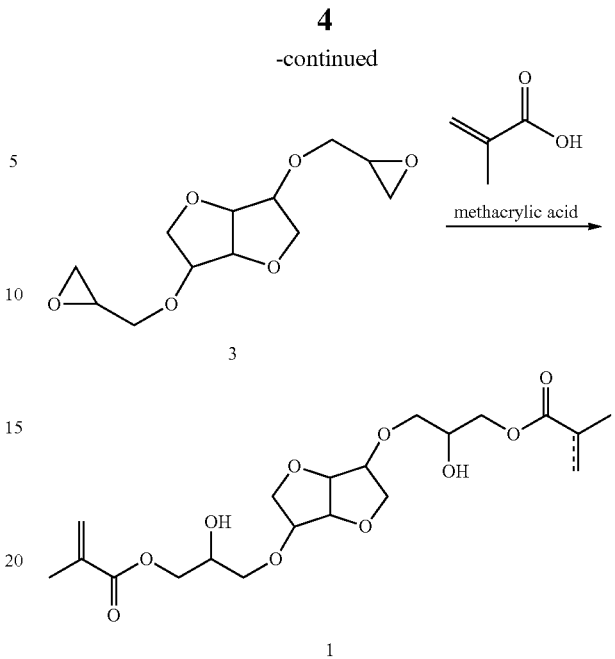

In the general aspect of the method, there is provided a method for preparing a compound denoted by the chemical formula 1 including the following step as in the reaction formula 1.

1) preparing a compound denoted by the following chemical formula 3 by reacting a compound denoted by the following chemical compound 2 and epihalohydrin under an existence of dehydrate; and 2) preparing a compound denoted by chemical formula 1 by reacting the compound denoted by the aforementioned chemical formula 3 and methacrylic acid.

[Chemical formula 1]

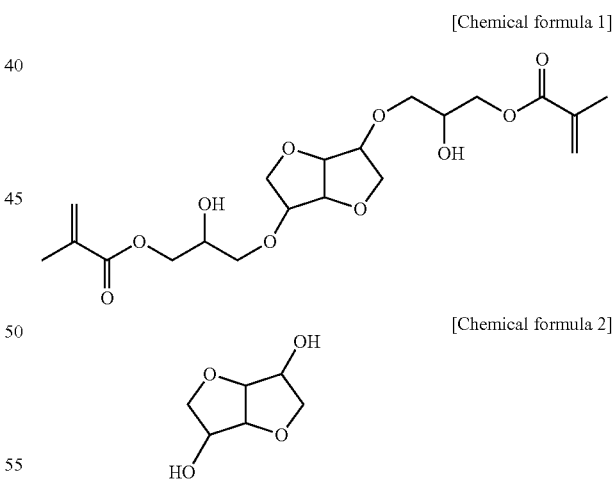

[Chemical formula 2]

[Chemical formula 3]

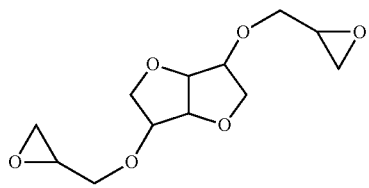

In the general aspect of the method, the step 1 may be a step of preparing a compound denoted by chemical formula 3 by reacting a compound denoted by chemical compound 2 and epihalohydrin under and existence of dehydrate, that is, applying a glycidyl functional group by reacting a DHH compound denoted by chemical formula 2 with epihalohydrin. This may be a process for effectively combining the glycidyl functional group to the DHH compound.

In the general aspect of the method, the compound denoted by the chemical formula 2 may be derived from carbohydrate polymer.

In the general aspect of the method, the compound denoted by the chemical formula 2 may be prepared from carbohydrate polymer as in the following reaction formula 2.

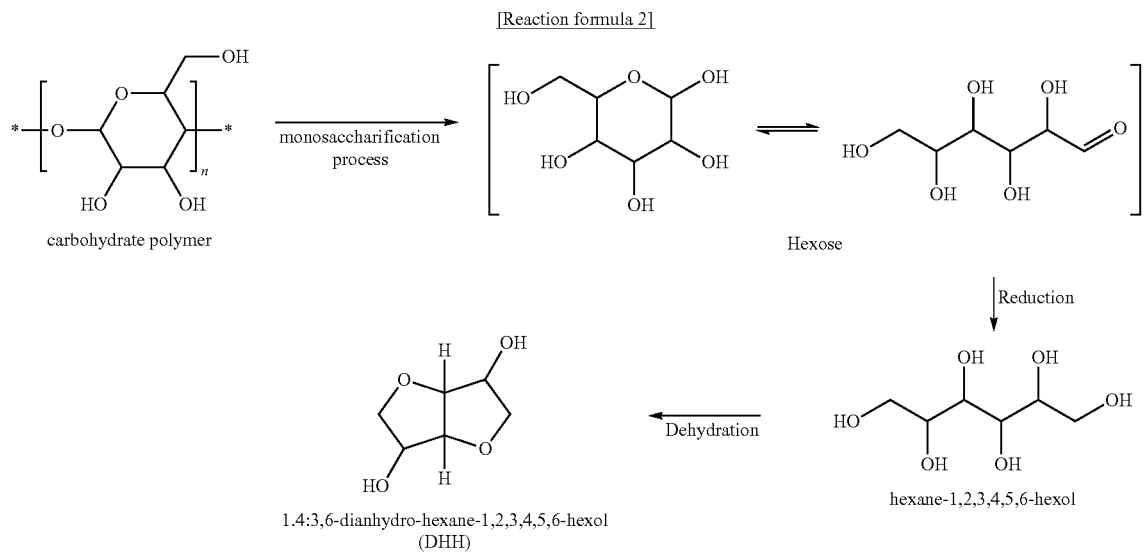

[Reaction formula 2]

1.4:3,6-dianhydro-hexane-1,2,3,4,5,6-hexol (DHH)

hexane-1,2,3,4,5,6-hexol

In the general aspect of the method, a DHH compound denoted by chemical compound 2 which is a heterocyclic compound where two 5-cycles are fused may be obtained, by extracting carbohydrate polymer such as cellulose which is approximately 30 to 40% of land plants, performing hydrolysis or saccharification of enzyme processing thereby obtaining a hexose compound, and then reducing the aldehyde group of the hexose compound through a hydrogenation process to prepare a hexane-1,2,3,4,5,6-hexol (HH) having six hydroxy groups, then cyclizing the HH compound through a dehydration reaction under an acid catalyst condition.

In the general aspect of the method, the step 1) may be performed by reacting the DHH compound (chemical compound 2) and epihalohydrin under an existence of dehydrate using aprotic polar solvent. This may provide a reaction condition where the glycidyl functional group may be easily combined with a secondary hydroxyl group that has a low reactivity in the DHH compound (chemical formula 2).

In the general aspect of the method, the aprotic polar solvent may be, but is not limited to, at least one selected from a group consisting of DMSO, DMF, DMA and NMP.

In the general aspect of the method, the epihalohydrin may be a compound where halogen atoms are combined with epoxide and adjacent carbon atoms, for example, it may be, but is not limited to, at least one selected from epichlorohydrin, epibromohydrin, and epiiodohydrin etc.

In the general aspect of the method, the dehydrate may consist of alkali metal and hydroxyl group, for example, it may be, but is not limited to, at least one selected from LiOH, NaOH, and KOH.

In the general aspect of the method, 100 to 800 parts by weight of epihalohydrin may be used for every 100 parts by weight of the compound denoted by chemical formula 2 of the step 1), and more preferably, 200 to 500 parts by weight of epihalohydrin may be used for every 100 parts by weight of the compound denoted by chemical formula 2 of the step 1). If less than 100 parts by weight of epihalohydrin is used, there is a disadvantage that the conversion ratio will fall, whereas if more than 800 parts by weight of epihalohydrin is used, there is a disadvantage of increased byproducts and the necessity to remove epihalohydrin.

In the general aspect of the method, 300 to 1000 parts by weight of dehydrate may be used for every 100 parts by weight of the compound denoted by chemical formula 2 of the step 1), and more particularly, 500 to 800 parts by weight of dehydrate may be used for every 100 parts by weight of the compound denoted by chemical formula 2 of the step 1). If less than 300 parts by weight of dehydrate is used, there is a disadvantage that the product yield rate will fall, whereas if more than 1000 parts by weight of dehydrate is used, there is a disadvantage of increased byproducts.

In the general aspect of the method, 200 to 2000 parts by weight of nonprotonic polar solvent may be used for every 100 parts by weight of the compound denoted by chemical formula 2 of the step 1), and more particularly, 300 to 1000 parts by weight of dehydrate may be used for every 100 parts by weight of the compound denoted by chemical formula 2 of the step 1).

In the general aspect of the method, a reaction time of the step 1) may be 0.5 to 16 hours, more particularly 3 to 8 hours. If the reaction time is shorter than 0.5 hour, there is a disadvantage that the conversion rate will fall, whereas if the reaction time is longer than 16 hours, there is a disadvantage of increased byproducts.

In the general aspect of the method, a reaction temperature of the step 1) may be 4 to 80° C., more particularly 30 to 50° C. If the reaction temperature is below 4° C., there is a disadvantage that the conversion rate will fall, whereas if the reaction temperature is above 80° C., there is a disadvantage of increased byproducts.

In the general aspect of the method, the step 2) may be a step for preparing a compound denoted by chemical formula 1 by reacting a compound denoted by chemical formula 3 with methacrylic acid, more particularly, providing two hydroxypropyl methacrylate (HPM) functional groups to a DHH frame by reacting a compound (chemical compound 3) having a DHH frame having 2 glycidyl functional groups with methacrylic acid.

In the general aspect of the method, the step 2) may be performed using triethylamine that is an organic base compound as a reaction catalyst.

In the general aspect of the method, 300 to 2000 parts by weight of methacrylic acid may be used for every 100 parts by weight of a compound denoted by chemical formula 3 of the step 2), and more particularly, 500 to 1000 parts by weight of methacrylic acid may be used for every 100 parts by weight of a compound denoted by chemical formula 3. If less than 300 parts by weight of methacrylic acid is used, there is a disadvantage that the product yield rate will fall, whereas if more than 2000 parts by weight of methacrylic acid is used, there is a disadvantage of having to remove unreacted methacrylic acid.

In the general aspect of the method, a reaction time of the step 2) may be 3 to 16 hours, more particularly 4 to 6 hours. If the reaction time is shorter than 3 hours, there is a disadvantage that the conversion rate will fall, whereas if the reaction time is longer than 16 hours, there is a disadvantage of increased byproducts.

In the general aspect of the method, a reaction temperature of the step 2) may be 80 to 120° C., more particularly 90 to 110° C. If the reaction temperature is below 80° C., there is a disadvantage that the conversion rate will fall, whereas if the reaction temperature is above 120° C., there is a disadvantage of increased byproducts.

In another general aspect, there is provided a photocurable composition comprising a compound denoted by the chemical formula 1 and a free-radical photoinitiator.

In the general aspect of the composition, the photocurable composition may be a solvent free type composition.

In the general aspect of the composition, the free-radical photoinitiator may be any type of free-radical photoinitiator, but more particularly, if it is at least one selected from a group consisting of benzophenon, benzoin, acetophenone, benzil, benzil ketal, anthraquineone, triphenylphosphine, benzoyl phosphine oxide, thioxanthone, xanthone, acridine derivative, penazine derivative, quinoxaline derivative, 1-penyl-1, 2-propanedione-2-O-benzoyloxim,1-aminophenyl ketone,1-hydroxyphenyl ketone, triazine compound and camphorquinone, the curing speed and characteristics may be further maximized In the general aspect of the composition, 0.1 to 10 parts by weight of free-radical photoinitiator may be used for every 100 parts by weight of a compound denoted by chemical formula 1, and more particularly, 0.5 to 5 parts by weight of free-radical photoinitiator may be used for every 100 parts by weight of a compound denoted by chemical formula 1. If less than 0.1 parts by weight of free-radical photoinitiator is used, there is a disadvantage that the product yield rate will fall, whereas if more than 10 parts by weight of free-radical photoinitiator is used, there is a disadvantage of not only deteriorating the curing speed but also economic feasibility due to excessive amount of free-radical photoinitiator.

In the general aspect of the composition, inorganic filler may be further included. It is effective that the inorganic filler is at least one of silica, alumina and talcum.

In the general aspect of the composition, various mixed additives such as release agents or pigments may be further included, for example silane coupling agent, stearic acid, palmitic acid, zinc stearate and calcium stearate.

In the general aspect of the composition, the various mixed additives may be prepared by sufficiently mixing and homogenizing them through a compressor, mixer or roller etc.

Dianhydrohexanehexol derivative, which is a photocurable compound having a biomass-derived DHH frame according to the present disclosure is capable of replacing a bisphenol A photocurable material which is a conventional material harmful to humans. It also has environmentally friendly advantages as it is derived from biomass instead of oil resources, and is responsive to high oil prices, and reduces emission of irreversible carbon dioxide.

In addition, the present disclosure is advantageous in that it discloses preparing a biomass-derived photocurable material with an excellent yield rate and synthesizing route. Another advantage is that it makes it possible to embody the same or higher level of properties of conventional photocurable materials derived from oil resources while having biomass as its raw material.

DETAILED DESCRIPTION

Figure 1:
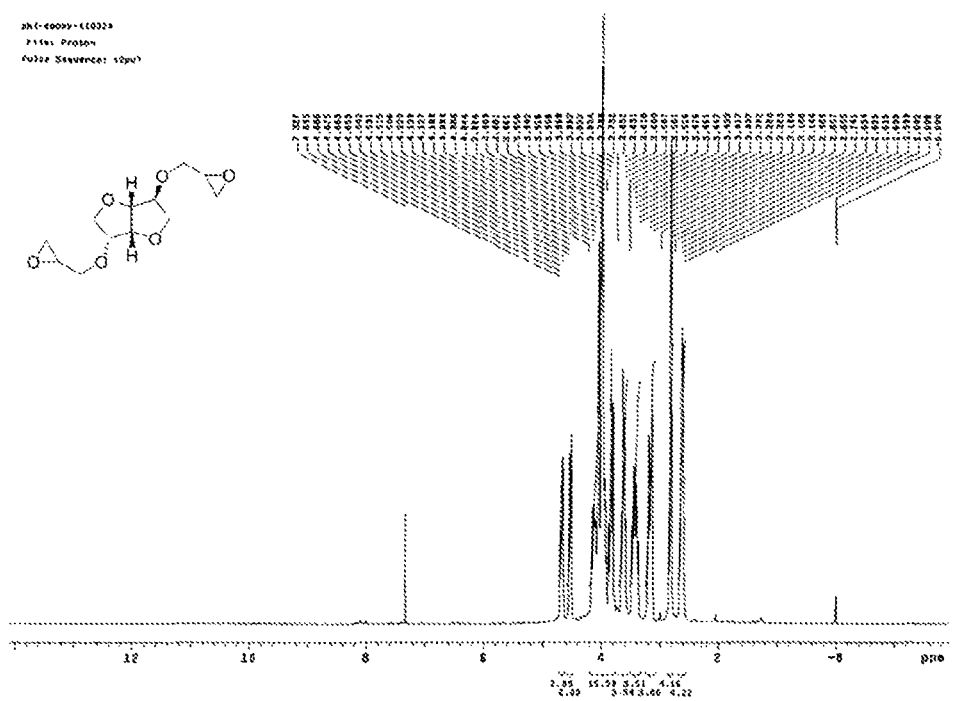
FIG. 1 is an H-NMR spectrum of a compound denoted by chemical formula 3.
Figure 2:
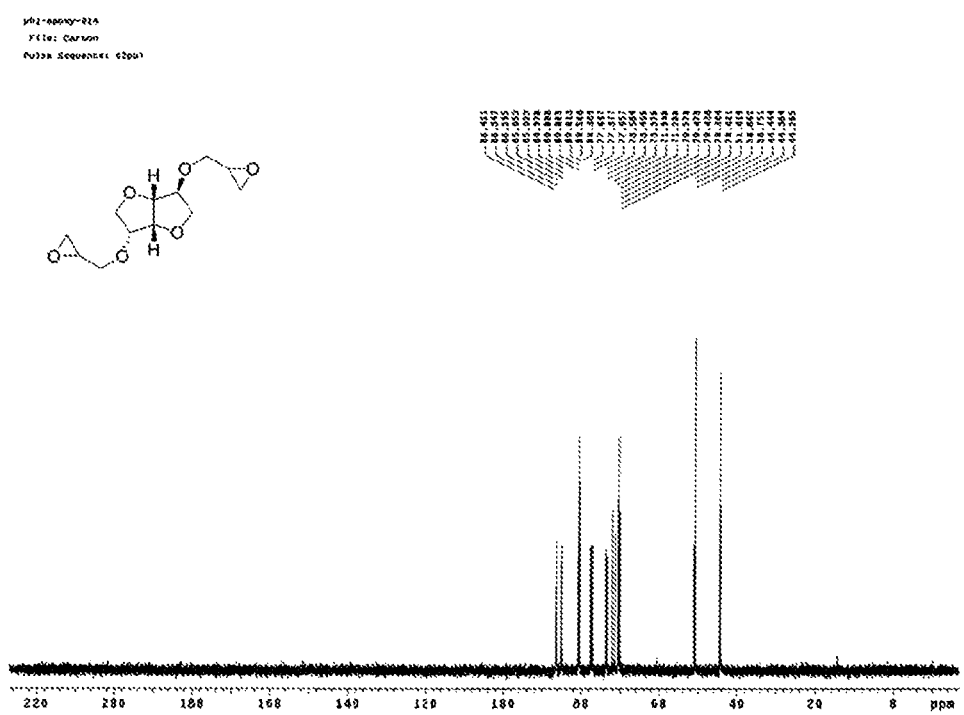
FIG. 2 is a C-NMR spectrum of a compound denoted by chemical formula 3.
Figure 3:
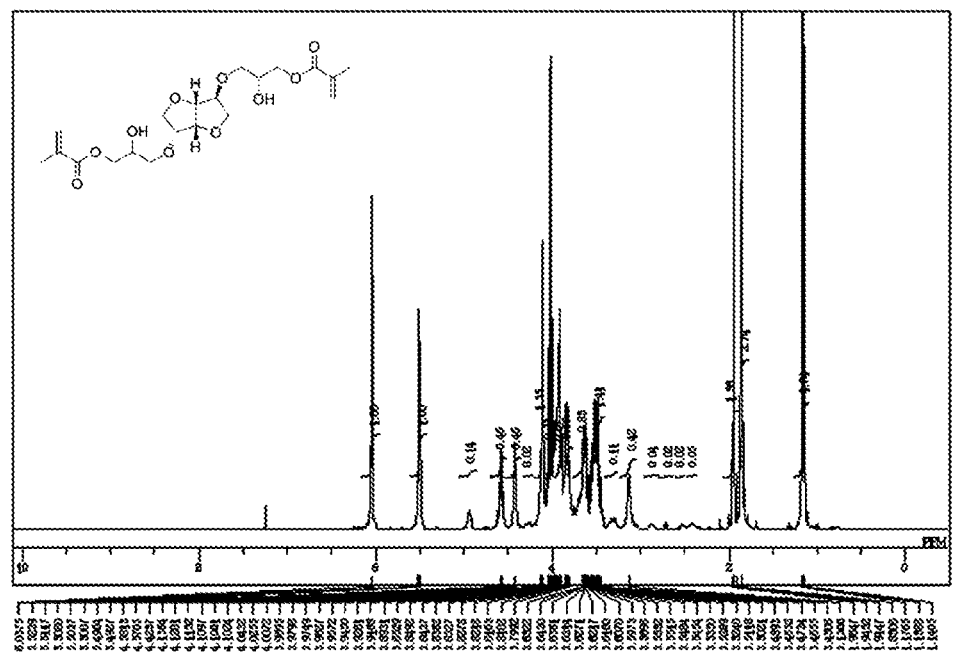
FIG. 3 is an H-NMR spectrum of a compound denoted by chemical formula 1.
Figure 4:
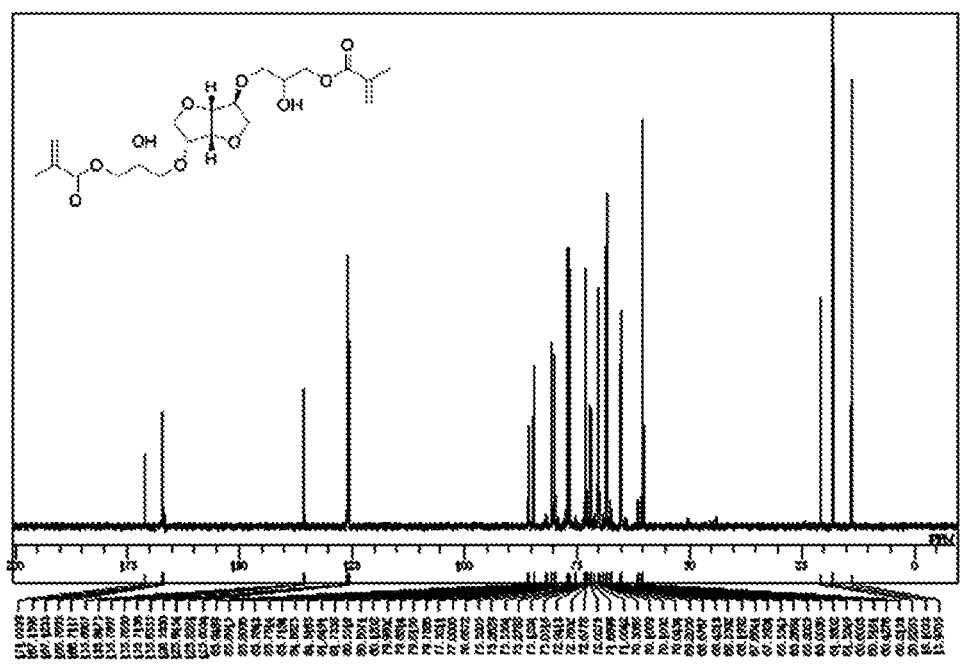
FIG. 4 is a C-NMR spectrum of a compound denoted by chemical formula 1.

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Exemplary Embodiment 1: Preparing a Photocurable Compound of the Present Disclosure Step 1: Preparing Diglycidyl Dianhydrohexanehexol

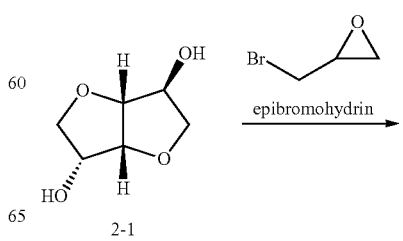

2-1

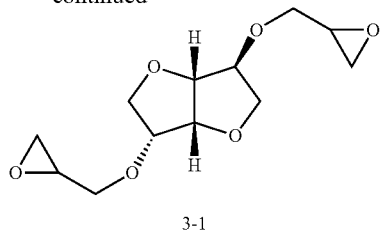

3-1

A compound of chemical formula 2-1 (5.0 g, 34 mmol) and KOH (14.0 g, 212 mmol) were put in a 100 mL round-bottom flask, and then the round-bottom flask was covered with a rubber stopper. Next, dry DMSO (25 mL) was added under a $N_2$ atmosphere. The round-bottom flask having the reaction solution was placed on a 24 bath, and a thermal equilibrium was conducted. When the thermal equilibrium was made inside the flask, epichlorohydrin (11.0 mL, 204 mmol) was slowly added using a syringe. Herein, the color of the suspension inside the flask gradually changed to dark brown as epichlorohydrin was added. After adding the epichlorohydrin, the reaction solution was stirred for 40 minutes to 6 hours so that the epichlorohydrin could react with the reaction solution. Next, the reaction solution was filtered through a syringe filter to remove salt in the remnants, and the filtrate was diluted with an appropriate amount of methylene chloride and then moved to an aliquot funnel. The reaction solution was then washed with distilled water followed by saline solution. Next, after moisture-removing, filtration and decompressed concentration of organic layers ($MgSO_4$), a transparent oil compound having chemical formula 3-1 (5.3 g, 20.4 mmole, 60%) was obtained through separation by flash chromatography (hexane:ethylacetate=1:1).

$^1$H NMR (600 MHz, $CDCl_3$): δ4.70-4.63 (m, H), 4.54-4.51 (m, H), 4.16-3.94 (m, 4H), 3.85-3.81 (m, 2H), 3.66-3.58 (m, 2H), 3.48-3.36 (m, 2H), 3.22-3.10 (m, 2H), 2.84-2.78 (m, 2H), 2.66-2.56 (m. 2H).

$^{13}$C NMR (150 MHz, $CDCl_3$): δ 86.1, 84.7, 80.5, 73.3, 73.0, 71.6, 70.9, 70.2, 50.6, 50.3, 44.1, 43.9.

Mass spectrum (ESI), m/z 259.1 (M+Na)$^+$.

Step 2: Preparing a Photocurable Compound of the Present Disclosure

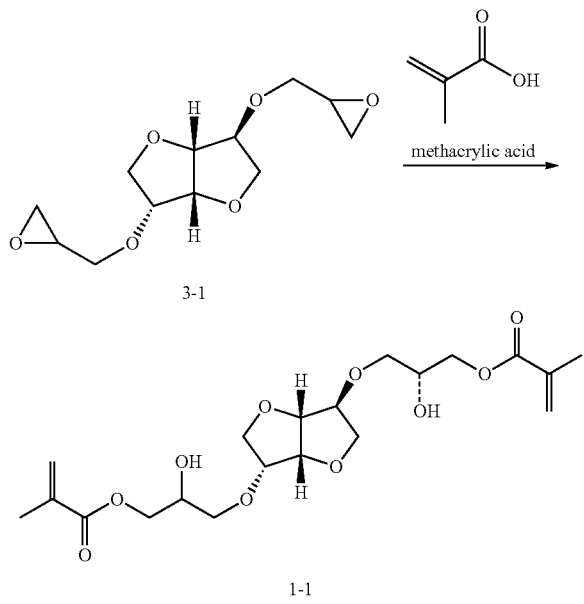

Under a nitrogen atmosphere, a compound of chemical formula 3-1 (1 g, 3.8 mmol) synthesized according to the aforementioned step 1, diphenylpicrylhydrazyl (10 mg, 0.6 mmol), and methacrylic acid (7 mL, 78 mmol) were added in a 100 mL round-bottom flask and then stirred. Next, 2-3 drops of TEA was added therein, and then stirred for 4 hours at 100° C. When the reaction finished, a dark brown reaction solution was obtained. This reaction solution was moved to an aliquot funnel and then washed for 4-5 times with 20 wt % $NaHCO_3$ solution, and then a work-up was carried out with water/ethyl acetate (water/E.A). The reaction solution was then collected in organic layer, distilled, and the solvent was removed. Next, a colorless compound having a viscosity of chemical formula 1-1 (1.23 g, 2.9 mmole, 75%) was obtained through a flash chromatography of hexane:ethylacetate (1:2, v/v).

$^1$H NMR (400 MHz, $CDCl_3$): δ 6.08 (s, 2H), 5.52 (s, 2H), 4.58 (s, 2H), 4.16 (s, 4H), 4.12-3.3 (m, 10H), 3.13 (s, 2H), 2.0 (s, 2H), 1.95 (s, 6H).

$^{13}$C NMR (100 MHz, $CDCl_3$): δ 171.0, 167.1, 135.8, 125.8, 85.8, 79.7, 75.2, 72.7, 70.0, 18.1.

Experimental Embodiment 1: Measurement of Photocurability Speed

A Photo-DSC is an apparatus having a photocurable accessory mounted onto a conventional DSC, the apparatus capable of ascertaining curing behaviors such as a conversion ratio and curing rate etc. by synchronizing the photocurable accessory and a conventional DSC. Q-1000 DSC of TA Instrument and Photocalorimetric accessory (Novacure 2100) were connected to each other and then used.

A medium pressure mercury lamp (100 W, Intensity: 20 mW/cm$^2$) was used as a light source, and TPO (2, 4, 6-Trimethylbenzoyl-diphenyl-dipheyyl Phosphine), which is a radical photocurable initiator, was used as a curing initiator. A specimen containing 1 wt % of photocurable initiator was put into an open type aluminum pan by approximately 4 mg at a time, and light was irradiated at 25° C., and then the reaction calorie caused by the specimen was measured.

As a result of analyzing the Photo-DSC, it could be seen that 90 equivalent % or more of photocuring was completed in 30 seconds.

Figure 5:
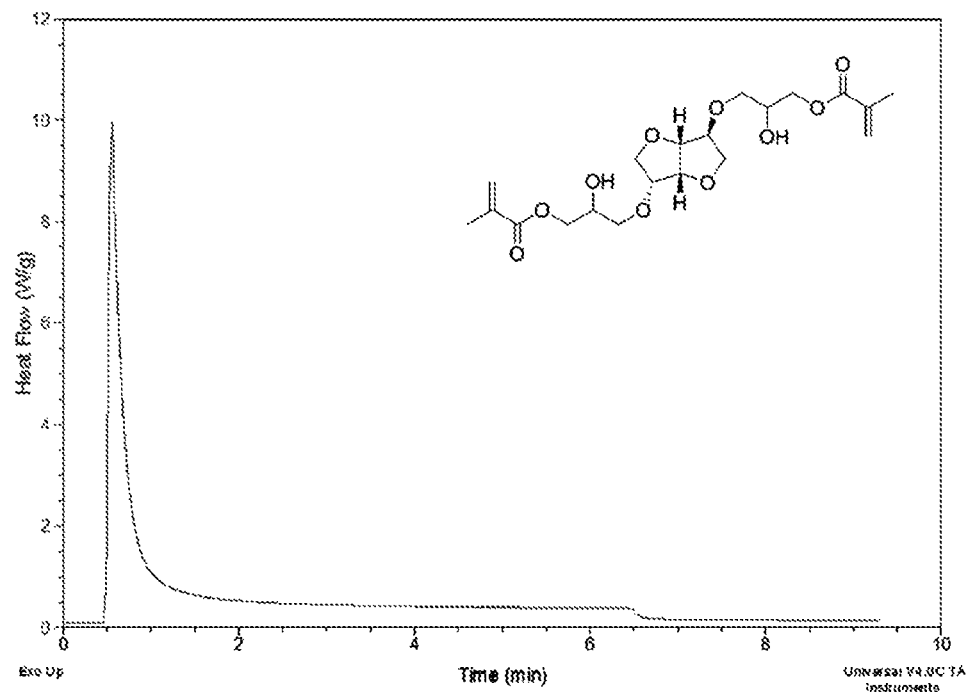
FIG. 5 illustrates measurement results of curing behavior made by Photo-DSC on a compound denoted by chemical formula 1.

The curing rate of the photocurable compound (exemplary embodiment 1) having a DHH frame by Photo-DSC is shown in FIG. 5.

Experimental Embodiment 2: measurement of photocurable contraction percentage

A photocurable contraction percentage was measured using a Linear Variable Differential Transformer (LVDT) transducer and UV Spot curing equipment. This is a method of evaluating a photocurable contraction percentage in the principle of measuring a linear variation of the contraction percentage which occurs while photocuring with a UV-Spot curing equipment.

For measuring a contraction percentage, the RB308 Linometer™ which is a Linometer System of R&B was used, and SP-7 of Ushio was used as the UV-Spot curing equipment. A stainless disk was placed on a non-contact linear displacement sensor with a certain distance, the sensor capable of measuring a distance using an electromagnetic field, and then a specimen of a certain thickness or a certain amount was loaded on the stainless disk. Next, the resin was covered with a slide glass and then fixated. Light source was fixated in a certain height in the slide glass, and when the sensor was activated at the same time UV was irradiated, the stainless disk rised in the direction of the slide glass, and the distance between the sensor and stainless disk increased. Herein, the increased distance was recorded, and the degree of contraction was measured.

When the specimen of 30 μL was irradiated in a distance of 10 cm using light source of an intensity of 1.2-1.5 mW/cm² and 1 wt % of TPO as the photocurable initiator, the result of measuring a photocurable contraction percentage of a photocurable compound having a DHH frame by a linear variable differential converter was 5.2 volume %.

Therefore, compared to (metha)cryl photocurable material showing approximately 10 volume % of photocurable contraction percentage, it has been determined that the photocurable compound of the present disclosure (exemplary embodiment 1) shows excellent performance. This seems to be because there exists an alkyl chain where the HPM functional group has a relatively higher degree of freedom compared to (metha)cryl functional group in terms of molecular structure.

Experimental Embodiment 3: Measurement of Lap Shear Strength

Lap shear strength is the most basic property of functions as an adhesive. In the present experiment, adhesive lap shear strength was measured using an UTM device. The device used in measuring the property was H100KS model of HOUNSFIELD, and the measured value was calculated using QMat (ver. 537) software.

As the subject of adhesion, transparent polycarbonate was used considering the light transmittance, and as a specimen, two subjects of adhesion having a certain size (1 inch×4 inch×0.12 inch=width×length×thickness) were arranged to overlap each other by an area of 1 inch×1 inch based on the ASTM D 5868-01 standard, and then an adhesive material was applied between the overlapped surface. When fixating each specimen to the UTM, each end of the grip was 1 inch, and the specimen was pulled by 0.5 inch/min speed, and then the shear strength was measured. A fixed amount of 20 μL was applied to each specimen, and was cured by irradiating UV in an intensity of 200 mW/cm² for a certain period of time.

As a result of irradiating UV for 30-300 seconds for each specimen and then curing the same, the adhesion lap shear strength was approximately 600–800 kPa, which is similar to that of the 1:1 mixture of Bis-GMA and TEGDMA currently on the markets. The measurement results of the adhesion strength are as shown in table 1 below.

TABLE 1

| Curing time (sec) | Adhesion lap shear strength (kPa) | |
| --- | --- | --- |
| | Photocurable compound of present disclosure (Exemplary embodiment 1) | Bis-GMA/TEGDMA (1:1) |
| 30 | 663 | 677 |
| 60 | 638 | 663 |
| 90 | 710 | 708 |
| 180 | 774 | 775 |
| 300 | 757 | 681 |

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

Industrial Applicability

The present disclosure is a dianhydrohexanehexol derivative of a photocurable compound having a DHH frame derived from biomass. It may replace bisphenol A photocurable material, and since it is derived from biomass instead of oil resources, it is responsive to high oil prices and can reduce emission of irreversible carbon dioxide, and thus has industrial applicability.

What is claimed is:
1. A compound represented by formula 1

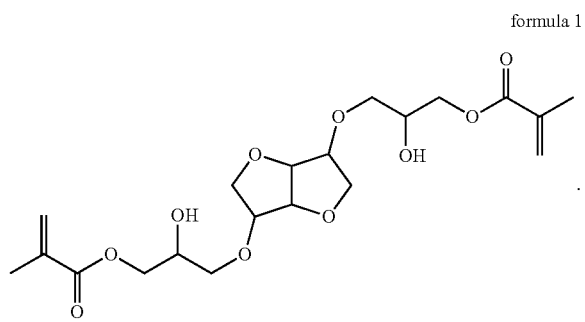 [SMILES: C=C(C)C(=O)OCC(O)COC1COC2C(OCC(O)COC(=O)C(=C)C)COC12]

2. A method for preparing the compound of formula 1

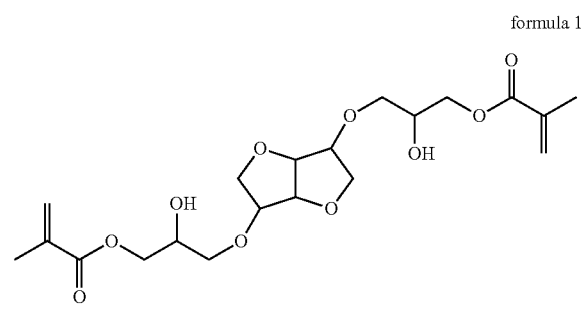 [SMILES: C=C(C)C(=O)OCC(O)COC1COC2C(OCC(O)COC(=O)C(=C)C)COC12]

comprising:
  a) reacting a compound of formula 2

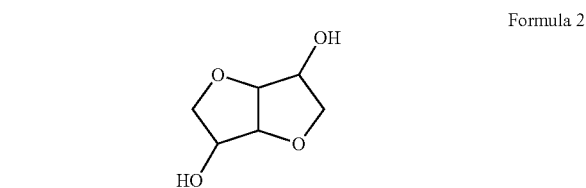

with epihalohydrin in the presence of a dehydrator to form a compound of formula 3; and

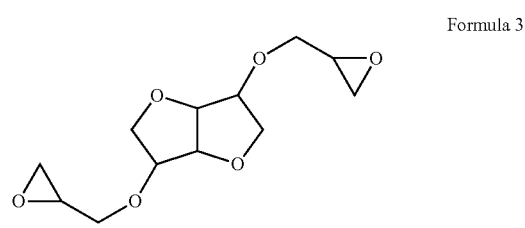 [SMILES: C1OC1COC1COC2C(OCC3CO3)COC12]

b) reacting the compound of formula 3 with methacrylic acid to form the compound of formula 1.
3. The method according to claim 2, wherein the compound of formula 2 is derived from carbohydrate polymer.

4. The method according to claim 2, further comprising a nonprotonic polar solvent in step a).

5. The method according to claim 4, wherein the nonprotonic polar solvent is selected from a group consisting of DMSO, DMF, DMA, and NMP or any combination thereof.

6. The method according to claim 2, wherein the epihalohydrin is selected from a group consisting of epichlorohydrin, epibromohydrin, and epiiodohydrin or any combination thereof.

7. The method according to claim 2, wherein the dehydrator is selected from a group consisting of LiOH, NaOH, and KOH or any combination thereof.

8. The method according to claim 2, wherein in step a) 100 to 800 parts by weight of epihalohydrin are used for every 100 parts by weight of the compound of formula 2.

9. The method according to claim 2, wherein in step a), 300 to 1000 parts by weight of epihalohydrin are used for every 100 parts by weight of the compound of formula 2.

10. The method according to claim 2, wherein step a) is carried out for about 0.5 to 16 hours.

11. The method according to claim 2, wherein step a) is carried out at a temperature between about 4 to 80° C.

12. The method according to claim 2, wherein step b) further comprises triethylamine.

13. The method according to claim 2, wherein in step b) 300 to 2000 parts by weight of methacrylic acid are used for every 100 parts by weight of the compound of formula 3.

14. The method according to claim 2, wherein a reaction time of step b) is between about 3 to 16 hours.

15. The method according to claim 2, wherein a reaction temperature of step b) is between about 80 to 120° C.

16. A photocurable composition comprising the compound of claim 1 and a free-radical photoinitiator.

17. The photocurable composition according to claim 16, wherein the photocurable composition is solvent free.

18. The photocurable composition according to claim 16, wherein the free-radical photoinitiator is selected from a group consisting of benzophenone, benzoin, acetophenone, benzil, benzil ketal, anthraquineone, triphenylphosphine, benzoyl phosphine oxide, thioxanthone, xanthone, acridine derivative, penazine derivative, quinoxaline derivative, 1-penyl- 1,2-propanedione-2-O-benzoyloxim,1-aminophenyl ketone, 1-hydroxyphenyl ketone, triazine compound and camphorquinone or any combination thereof.

19. The photocurable composition according to claim 16, wherein 0.1 to 10 parts by weight of free-radical photoinitiator are used for every 100 parts by weight of the compound of formula 1.

20. The photocurable composition according to claim 16, further comprising an inorganic filler.

* * * * *